(12) United States Patent
Takeo

(10) Patent No.: US 6,199,695 B1
(45) Date of Patent: Mar. 13, 2001

(54) CONTAINER FOR INTERDENTAL CLEANER

(76) Inventor: Komamura Takeo, 3-207, Kanasugi, Chiba-ken, Matsudo-shi (JP)

( * ) Notice: Subject to any disclaimer, the term of this patent is extended or adjusted under 35 U.S.C. 154(b) by 0 days.

(21) Appl. No.: 09/396,167

(22) Filed: Sep. 14, 1999

(51) Int. Cl.[7] .................................................. B65D 85/20
(52) U.S. Cl. ............................................. 206/380; 206/37
(58) Field of Search .................................... 206/380, 382, 206/37; D3/201, 205, 207; 132/321, 328, 329; 433/141, 143

(56) References Cited

U.S. PATENT DOCUMENTS

| | | | | |
|---|---|---|---|---|
| 469,064 | * | 2/1892 | McKay | 206/380 X |
| 647,187 | * | 4/1900 | Knapp | 206/380 |
| 2,877,892 | * | 3/1959 | Severson | 206/37 X |
| 4,040,433 | * | 8/1977 | Edison | 132/321 |
| 4,269,313 | * | 5/1981 | Smith | 206/380 |
| 5,419,346 | * | 5/1995 | Tipp | 132/329 |

FOREIGN PATENT DOCUMENTS

277953 * 9/1951 (CH) ..................................... 206/382

* cited by examiner

*Primary Examiner*—Bryon P. Gehman
(74) *Attorney, Agent, or Firm*—Jordan and Hamburg LLP

(57) ABSTRACT

A holder includes a plate-like body having a recess formed therein, the recess being configured to leave a holding portion for the body of the toothpick-like interdental cleaner. The holder portion includes a fitting groove, adapted to removably secure the body of the interdental cleaner along a longitudinal direction thereof when received therein. When so received, the toothpick-like interdental cleaner is restrained at the intermediate portion of its body, and its extreme ends, positioned within the recess, do not come in contact with any interior surfaces, thereby being kept clean. A case is further provided for receiving the holder.

4 Claims, 3 Drawing Sheets

CONTAINER FOR INTERDENTAL CLEANER

BACKGROUND OF THE INVENTION

The present invention relates to a container for an interdental cleaner, and more particularly, a combination of a holder for containing and holding a toothpick-like cleaner to clean up between teeth and a case thereof.

A toothpick or other similar device for interdental cleaning (hereinafter, collectively referred to as a "toothpick-like interdental cleaner" or simply "interdental cleaner") has been heretofore used in order to remove plaque or bits of food stuck between teeth. Although there have been various type toothpick-like interdental cleaners that are not a simple linear toothpick, but rather which have a structure in which ends are different from each other and so on, a case capable of containing and carrying these tooth cleaners has heretofore not been adequately developed.

SUMMARY OF THE INVENTION

A holder is provided in the form of a plate-like body having a length and a width at least greater than those of an interdental cleaner. A recess is formed in the body, leaving a holding portion for the body of the interdental cleaner disposed in a position corresponding approximately to the longitudinal middle of the plate-like body. The holding portion is formed with a fitting groove, adapted to be fitted with the body of the interdental cleaner along the longitudinal direction. Thus, the toothpick-like interdental cleaner is removably held at the intermediate portion of its body, and its extreme ends positioned within the recess do not come in contact with any interior surfaces, thereby being kept clean. Such a structure is extremely useful for an interdental cleaner having a bent portion at an extreme end.

A case is formed as a tubular body having a length at least long enough to contain the holder, and is advantageously made separable along the longitudinal direction. Thus, the case can be dismantled after use over a certain period of time to get rid of waste, dust or the like which collects in the innermost recess.

In accordance with a further embodiment, fitting grooves are formed at the holding portion of the holder which are offset to each other on the face side and the reverse side of the holding portion. Therefore, two toothpicks can be held within a holder. In addition, such a structure in which the fitting grooves are formed in an offset manner enables the holder to be made thinner and convenient for carrying, and fitting and removing of the interdental cleaner is facilitated since the interdental cleaners can be easily accessed by the fingers.

In a further embodiment, a clip formed in the above-mentioned case or the holder is provided which may be connected to a breast pocket or the like, thus making a container for the interdental cleaner more convenient for carrying.

In accordance with yet another embodiment, engaging protrusions on both sides of a longitudinal end of the holder are formed for engaging grooves adapted to the engaging protrusions within the interior of the case, and a notch is provided having a width at least greater than the thickness of the holder at a part of an opening of the case. Accordingly, when the holder is taken out of the case, the engaging protrusion and the engaging groove are engaged, thereby preventing the holder from popping out abruptly. In addition, the holder can stand on the case by virtue of the notch, which prevents a contact of the holder with a table or the like. Thereby, the cleanliness of the holder and the toothpick-like interdental cleaner can be maintained.

DETAILED DESCRIPTION OF THE INVENTION

Figure 1:
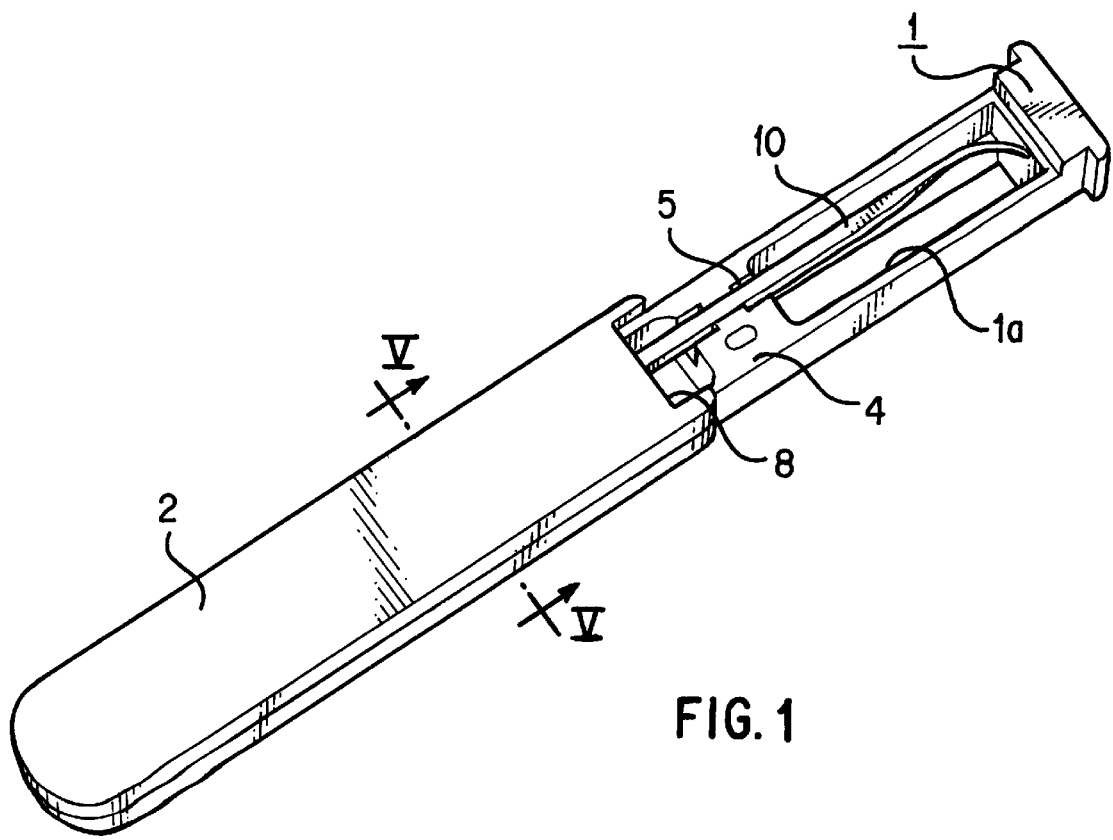
FIG. 1 is a perspective view of a holder and a case according to an embodiment of the present invention.

As shown in FIG. 1, a case 2, made of a synthetic resin or the like, is provided in the form of a flat, square-shaped tubular body having a length and a width at least long enough to contain a toothpick-like interdental cleaner 10. The case 2 has a substantially rectangular shape in cross section, a closure on one edge and an opening on the other edge.

Figure 2:
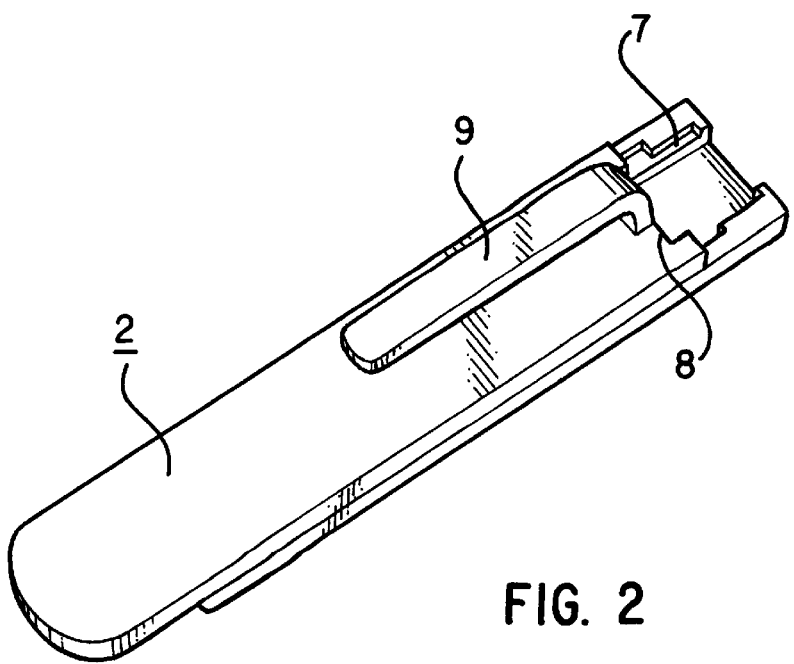
FIG. 2 is a perspective view showing an example of a case being made separable.

With the above-mentioned structure as the basic embodiment, another embodiment of a case 2 is as shown in FIG. 2, wherein a side is split along the longitudinal direction thereby creating a pair of separate components which are slidably engaged with one another for opening and closure. With such a structure, removal of waste, dust or the like collecting in the innermost recess of the case 2 can be easily carried out following use for a certain period of time.

Figure 3:
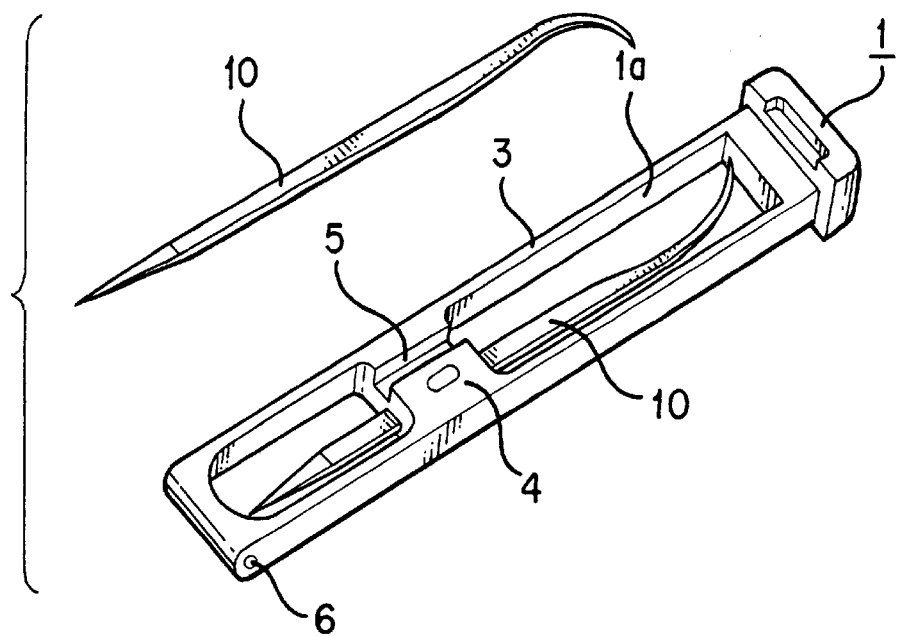
FIG. 3 is a perspective view of a holder.

As shown in FIG. 1 and FIG. 3, a holder 1 is also provided which has a length and a width at least greater than those of the toothpick-like interdental cleaner 10, and includes a plate-like body 3 made of a synthetic resin or the like, having a thickness which allows the plate-like body 3 to be slidably received in and held in the case 2. A head to be engaged in the opening face of the case 2 is formed on one longitudinal end of the plate-like body 3. A recess 1a is formed in such a manner that a holding portion 4 is left which interrupts the recess approximately at the middle of the plate-like body 3. This recess 1a may be a hollow region extending entirely through the plate-like body 3 as depicted in the embodiments of the drawings.

The holding portion 4 of the holder 1 is integrally formed to extend toward the center of the longitudinal intermediate position of the plate-like body 3 and a fitting groove 5 is formed along the longitudinal direction of the plate-like body 3. The toothpick-like interdental cleaner 10 is fitted in the fitting groove 5, securing same. The extreme ends of the toothpick-like interdental cleaner 10 are positioned and contained within the recess 1a of the plate-like body 3. By forming the holding portion 4 at a position corresponding with approximately the middle of the plate-like body 3, the toothpick-like interdental cleaner 10 can be held at the intermediate portion of its body. Therefore, the extreme ends do not come into contact with any interior surfaces even while being contained in the holder 1, and the cleanliness thereof can be maintained. Such a structure is extremely useful for an interdental cleaner having a bent portion at an extreme end, as shown in the examples depicted in the figures.

The fitting groove 5 is formed with a width substantially the same as the diameter of the interdental cleaner 10. The interdental cleaner 10 is fitted and maintained in place by elasticity. In order to improve a stopping force, a plurality of convex structures may be formed in the interior of the fitting groove 5. A claw or the like may be formed at a portion of the interior of the fitting groove 5 to provide a structure to hold the interdental cleaner 10. It is further noted that any alternative structure is also deemed suitable if it holds an intermediate portion of the body of the interdental cleaner 10.

A head provided as a lid-shaped portion of the holder 1, is configured to be fitted with the opening face of the case 2, or a notch 8 thereof when it is formed in a case 2, as described below. This configuration is for purposes of preventing waste, dust or the like from entering the case 2 while the holder 1 is in the case 2 in a contained state.

According to a further embodiment of the present invention, as clarified in FIG. 3, fitting grooves 5 are formed offset to each other on the face side and the reverse side of the plate-like body 3 to provide a structure enabling two toothpick-like interdental cleaners 10 to be held. With such a structure, the plate-like body 3 is kept thinner, and fingers are easily inserted to conveniently take out the toothpick-like interdental cleaner 10, since the toothpick-like interdental cleaner 10 is drawn to either the right or left side relative to the plate-like body 3 when being fitted.

A holder 1 with which a toothpick-like interdental cleaner is fitted, is inserted and contained in a case 2 having the foregoing structure. It is preferable to adapt a structure in which the case 2 and the holder 1 do not easily slide apart from each other by means of suitable elasticity. In the present embodiment, since an engaging protrusion 6 formed in the holder 1 is stopped at the end of an engaging groove 7 which stops at the opening of the case 2, as shown in FIG. 2, the holder does not easily pop out from the case 2. A pin-like stopping member may be used for stopping the case 2 and the holder 1.

Since the toothpick-like interdental cleaner 10 is used in people's mouths, it is preferable to use an antibacterial material for the case 2 and the holder 1.

Moreover, it is extremely convenient if a clip 9 which permits connection to a breast pocket or the like as an ordinary pen is formed in the case 2 as shown in FIG. 2 or the holder 1 (not shown).

Further, in order to add to the convenience of the present invention, an engaging protrusion 6 is formed on both widthwise sides of the edge of the holder 1 (the edge not formed with a lid portion), an engaging groove 7 adapted to said engaging protrusion 6 in the interior of the opening of the case 2 and a notch 8 having a thickness at least greater than that of said holder 1 at a part of the opening of the case 2, as shown in FIG. 3. The engaging protrusion 6 slides along said engaging groove 7 allowing sliding of the holder 1 in and out.

Figure 4:
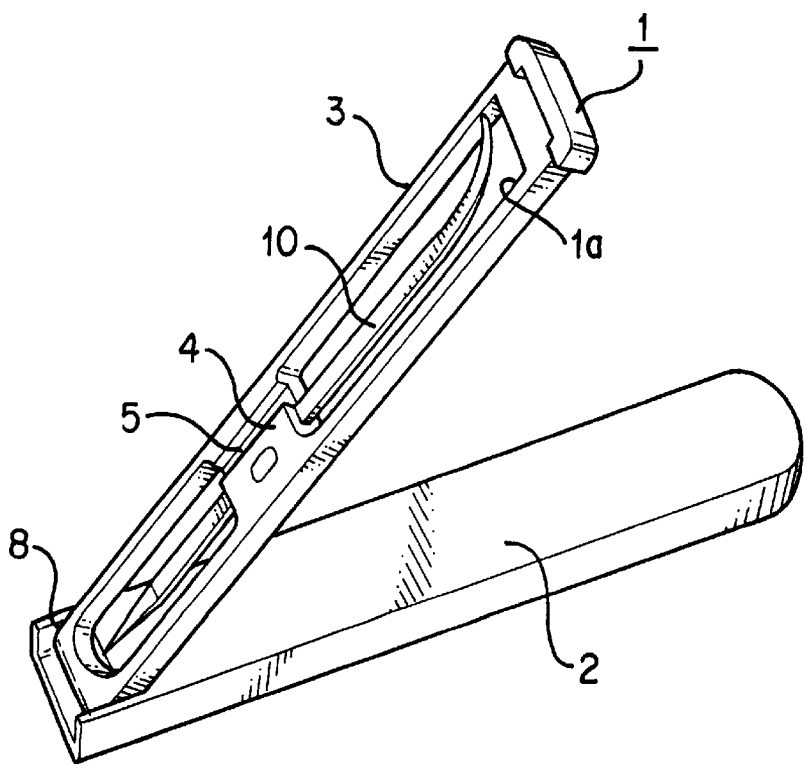
FIG. 4 is a perspective view depicting a standing state of a holder on a case.
Figure 5:
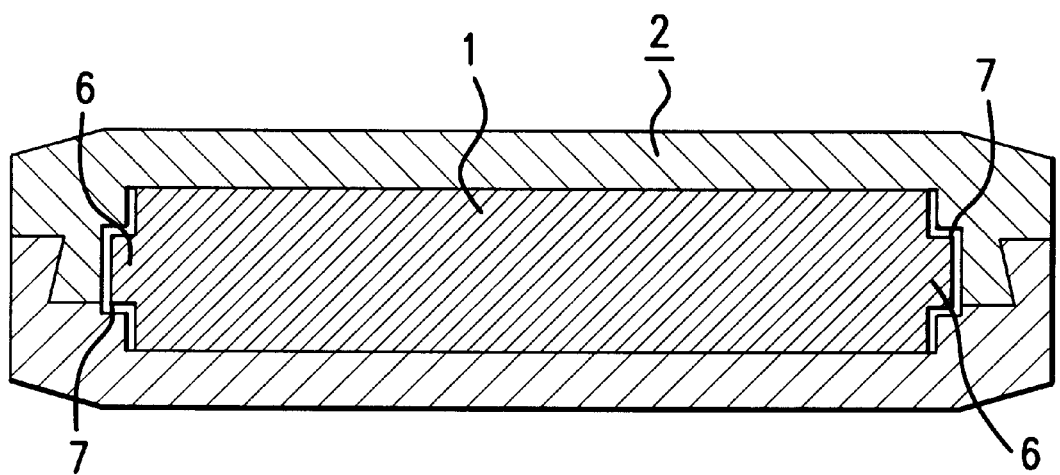
FIG. 5 is a cross-sectional view taken on line V—V of FIG. 1.

With such a structure, the holder 1 does not pop out abruptly when removed from the case 2, because the engaging groove 7 is formed up to the opening of the case 2 to stop the engaging protrusion 6 around the opening of the case 2. Also, since the notch 8 is formed in the case 2, when the holder 1 is erected in an abutting state of the fitting protrusion 6 with the end of the fitting groove 7, it is possible to stand the holder 1 on the case 2, as shown in FIG. 4. Accordingly, by standing the holder 1 during use of the toothpick-like interdental cleaner 10, the holder 1 is prevented from coming into a contact with a table or the like, whereby it is possible to keep the holder 1 and the toothpick-like body 10 clean.

What is claimed is:

1. A container for an interdental cleaner which includes a body portion disposed intermediate of opposed longitudinal ends thereof, comprising:

a holder including a body, said body including a recess suitably dimensioned to receivably accommodate the interdental cleaner, said recess being configured to leave a holding portion disposed in a position corresponding approximately to a longitudinal middle of said body, said holding portion including a fitting groove which runs along a longitudinal direction of said body and is open to a side of said holding portion facing outwardly in a direction orthogonal to said longitudinal direction, and which is configured to removably secure the body portion of the interdental cleaner when received in said recess; and a case including a tubular body suitably dimensioned to receivably contain the holder.

2. The container according to claim 1, wherein said case is comprised of two assembled components separable along a dividing locus extending in a longitudinal direction of said case.

3. A container for an interdental cleaner which includes a body portion disposed intermediate of opposed longitudinal ends thereof, comprising:

a holder including a body, said body including a recess suitably dimensioned to receivably accommodate the interdental cleaner, said recess being configured to leave a holding portion disposed in a position corresponding approximately to a longitudinal middle of said body, said holding portion presenting a face side directed orthogonally outward relative a longitudinal direction of said body and a reverse side disposed on a side thereof opposed to said face side, said holding portion including at least two fitting grooves which runs along said longitudinal direction of said body and which are configured to removably secure the body portion of the interdental cleaner when received in said recess, the recess being formed as a hollow extending entirely through said body in said direction orthogonal to said longitudinal direction, and a one of said at least two fitting grooves being formed on the face side of said holding portion and another of said at least two fitting grooves being formed on the reverse side of the holding portion; and a case including a tubular body suitably dimensioned to receivably contain the holder.

4. The container according to claim 1, 2, or 3, wherein:

said holder includes a longitudinal end presenting opposed sides on which engaging protrusions are formed;

an interior of said case includes engaging grooves engageable by said engaging protrusions; and said case includes an opening at a longitudinal end thereof, said case further including a notch formed at said opening having a width at least greater than a thickness of said holder.

* * * * *